US00PP35896P2

(12) United States Plant Patent
Muñoz et al.

(10) Patent No.: US PP35,896 P2
(45) Date of Patent: Jul. 2, 2024

(54) BLUEBERRY PLANT NAMED 'FL17-141'

(50) Latin Name: ***Vaccinium corymbosum* L.**
Varietal Denomination: FL17-141

(71) Applicant: Florida Foundation Seed Producers, Inc., Marianna, FL (US)

(72) Inventors: Patricio Muñoz, Gainesville, FL (US); James W. Olmstead, Aptos, CA (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 5 days.

(21) Appl. No.: 18/473,003

(22) Filed: Sep. 22, 2023

(51) Int. Cl.
*A01H 5/08* (2018.01)
*A01H 6/36* (2018.01)

(52) U.S. Cl.
USPC ..... Plt./157

(58) Field of Classification Search
USPC ..... Plt./156, 157
See application file for complete search history.

(56) References Cited

U.S. PATENT DOCUMENTS

PP12,165 P2 10/2001 Lyrene

OTHER PUBLICATIONS

U.S. Appl. No. 18/473,008, filed Sep. 22, 2023, Muñoz et al.

*Primary Examiner* — Karen M Redden
(74) *Attorney, Agent, or Firm* — Dentons US LLP

(57) ABSTRACT

'FL17-141' is a new and distinct southern highbush blueberry (*Vaccinium corymbosum* L.) variety distinguished at least by a none to low chilling requirement, vigorous and healthy, semi-upright growth habit with good evergreen production, high early yield, good field disease resistance, and large fruit that are moderately sweet with high wax cover and exhibit small picking scars.

6 Drawing Sheets

Latin name of the genus and species of the plant claimed: *Vaccinium corymbosum* L.

Variety denomination: 'FL17-141'.

BACKGROUND OF THE INVENTION

The invention relates to a new and distinct hybrid variety of southern highbush blueberry (*Vaccinium corymbosum* L.) plant 'FL17-141'. 'FL17-141' originated as a seedling that was generated from a cross performed in Gainesville, FL during February of 2014 between 'FL14-28' (unpatented), as the female (seed) parent, and 'FL13-212' (unpatented), as the male (pollen) parent. The seedling was planted in a high-density field nursery in May 2015, and the first fruit were evaluated in April of 2016. 'FL17-141' was first asexually propagated during 2017 by softwood stem cuttings in Gainesville, FL. After the second year of fruiting in the field, 'FL17-141' was propagated by softwood stem cuttings during the spring of 2017 to establish an experimental 15-plant test plot for a variety test that was conducted during January of 2018 in Waldo, FL and a 5-plant test plot in Arcadia, FL. It was during this variety test that the experimental code 'FL17-141' was assigned. Based on the growth, yield and fruit quality of this plot, 'FL17-141' was repropagated by softwood stem cuttings and additional experimental test plots ranging from 5 to 45 plants were established for experimental research trials throughout Florida. These plots have been observed during flowering and ripening each year since establishment, and no mutations or off-type plants have been observed.

SUMMARY OF THE INVENTION

'FL17-141' differs from its parents and all other known southern highbush blueberry plants. The following are the most distinguishing characteristics of 'FL17-141' when grown under normal horticultural practices in Florida: (1) a low to no chilling requirement, particularly for the flower buds; (2) a vigorous, semi-upright growth habit; (3) high yield during the months of March and April; (4) large, firm, sweet berries that exhibit small picking scars and strong waxy cover; and (5) extended tested postharvest fruit quality holding for up to 49 days.

'FL17-141' plants can be readily and unambiguously distinguished from those of its parents at least based upon earliness, higher yield, and quality of fruit. The early fruit yield exhibited by plants of 'FL17-141' is significantly earlier and higher yielding than that of either 'FL14-28' and 'FL13-212'.

Blueberry variety 'Emerald' (U.S. Pat. No. 12,165) is planted throughout the southeastern United States. Plants of 'FL17-141' and 'Emerald' can be readily and unambiguously distinguished at least based upon growth habit, the time at which their fruit is produced, as well as their fruit size and cluster tightness. Plants of 'FL17-141' display a more upright growth habit than 'Emerald'. Plants of 'FL17-141' produce their fruit significantly earlier than those of 'Emerald' when no growth regulator is used, and the fruit of 'FL17-141' are larger, uniform, and with looser clusters compared to 'Emerald'.

BRIEF DESCRIPTION OF THE DRAWINGS

'FL17-141' is illustrated in the accompanying photographs, which show the plant's flowers, fruit, leaves, and form. Colors shown are as true as can be reasonably reproduced by photographic procedures and may differ from those cited in the detailed description, which accurately describe the colors of 'FL17-141'.

DETAILED BOTANICAL DESCRIPTION

Figure 1:
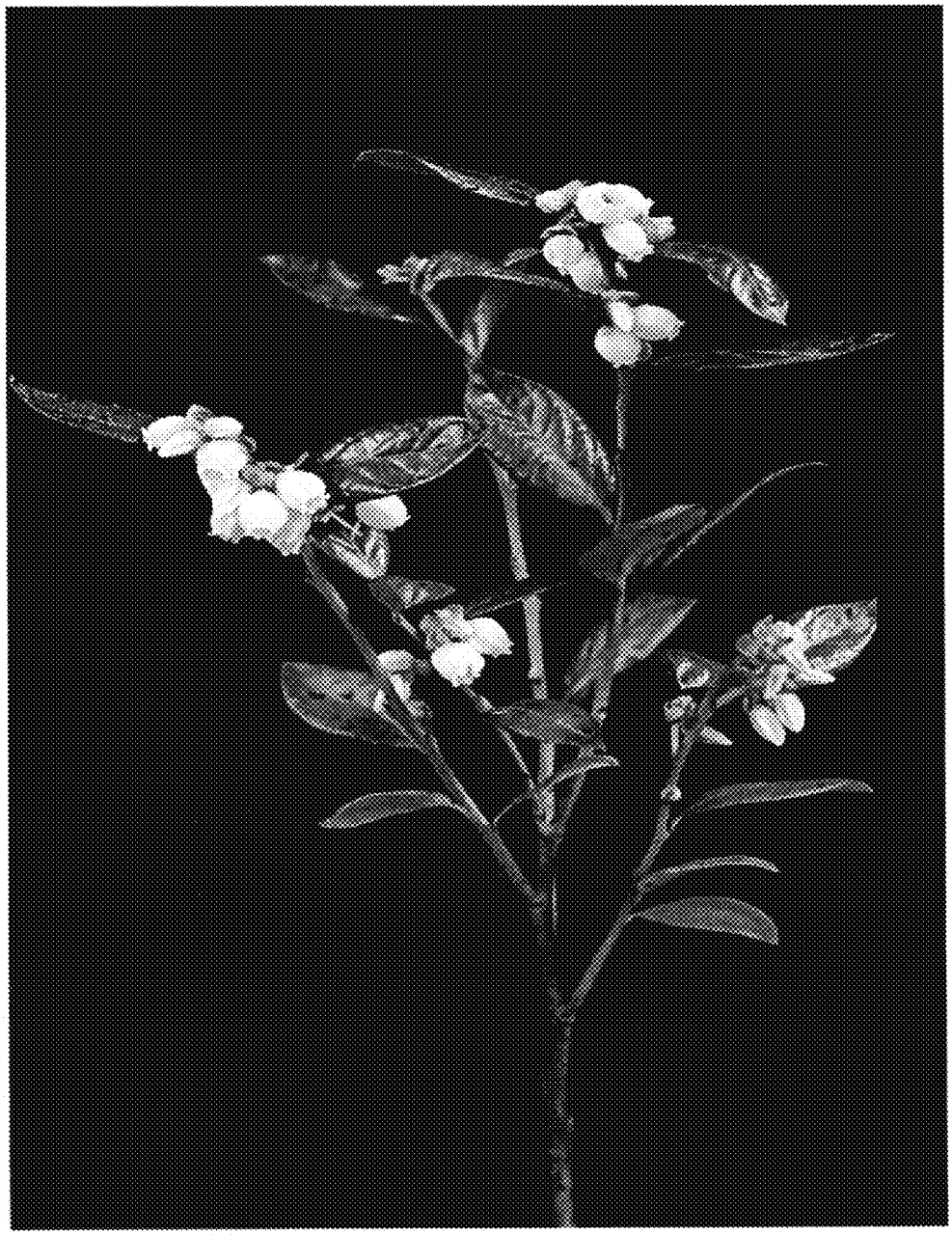
FIG. 1—Shows clusters of opening 'FL17-141' flowers.
Figure 2:
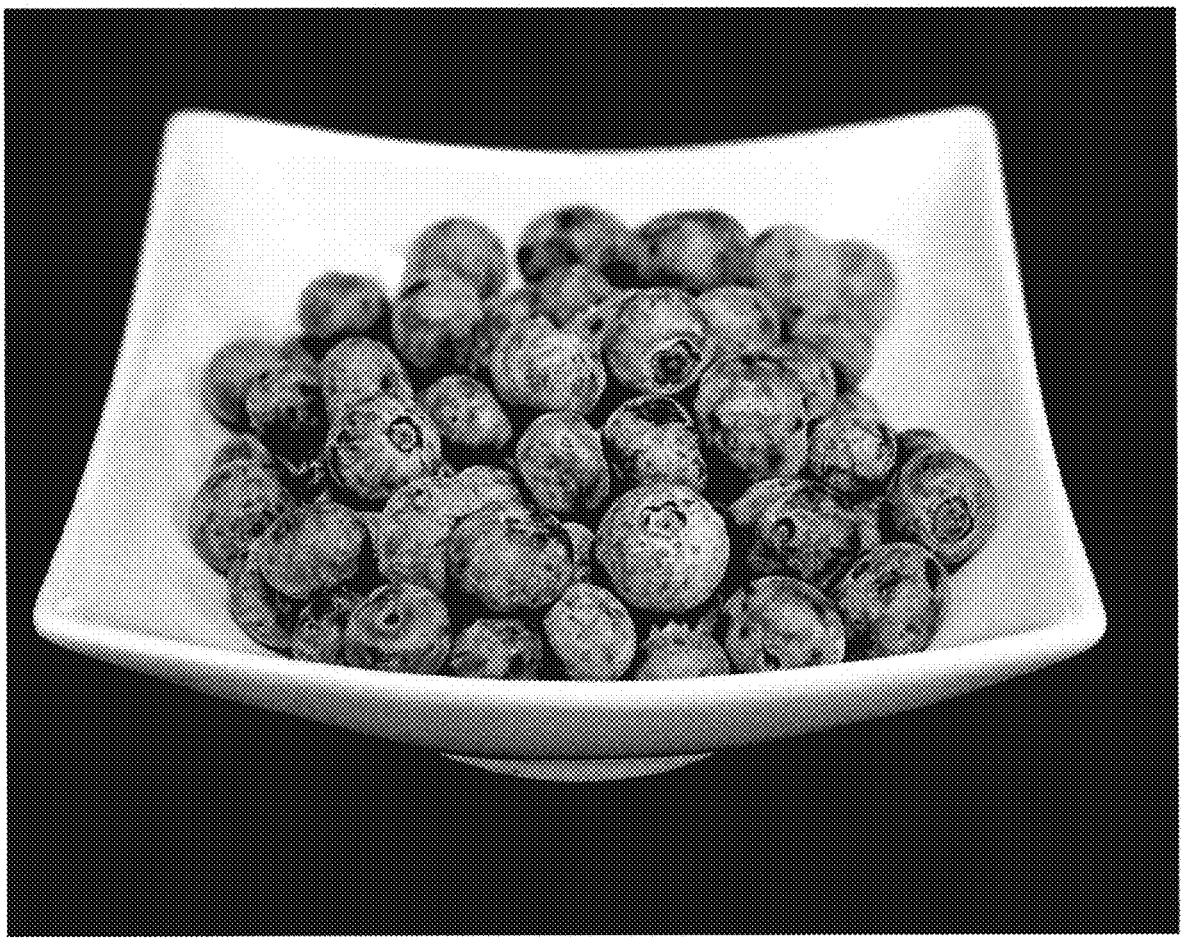
FIG. 2—Shows a close-up of harvested 'FL17-141' berries.
Figure 3:
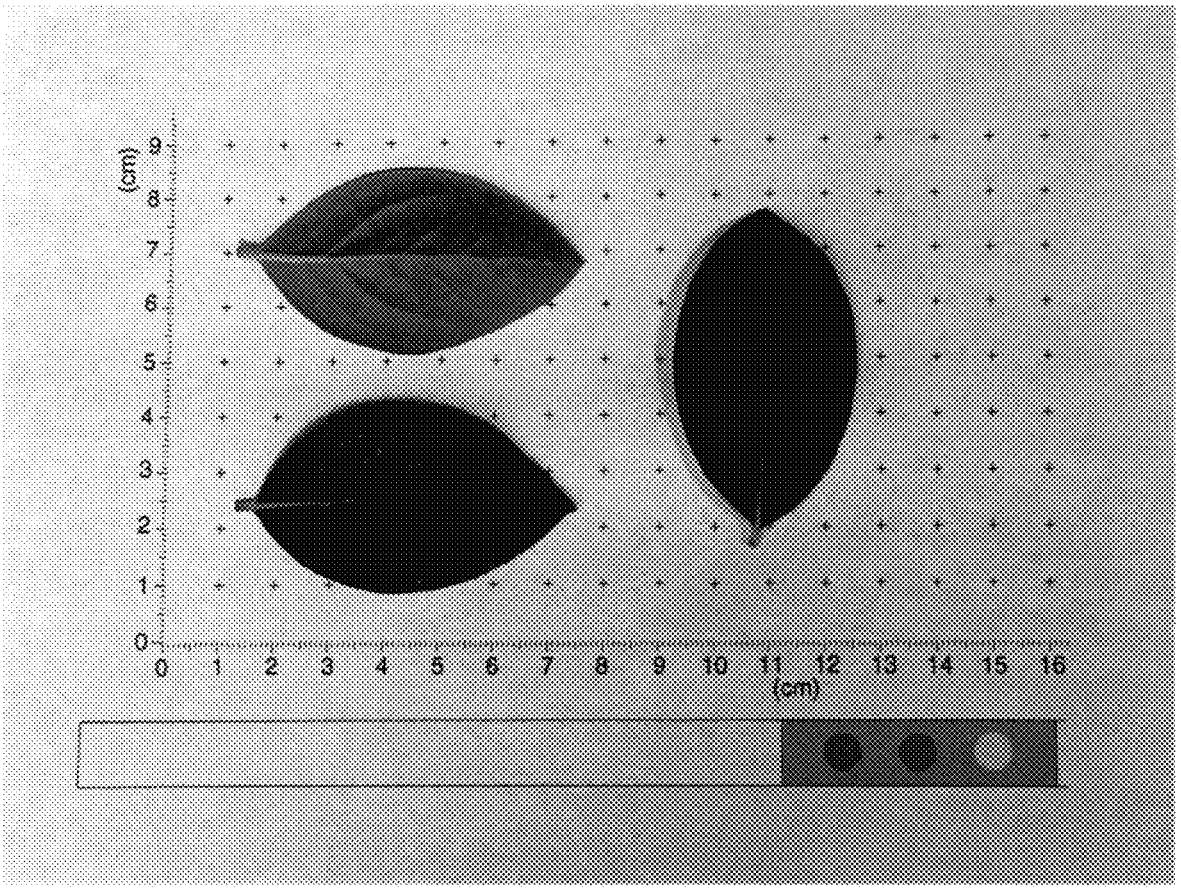
FIG. 3—Shows a close-up of mature 'FL17-141' leaves with a scale bar.
Figure 4:
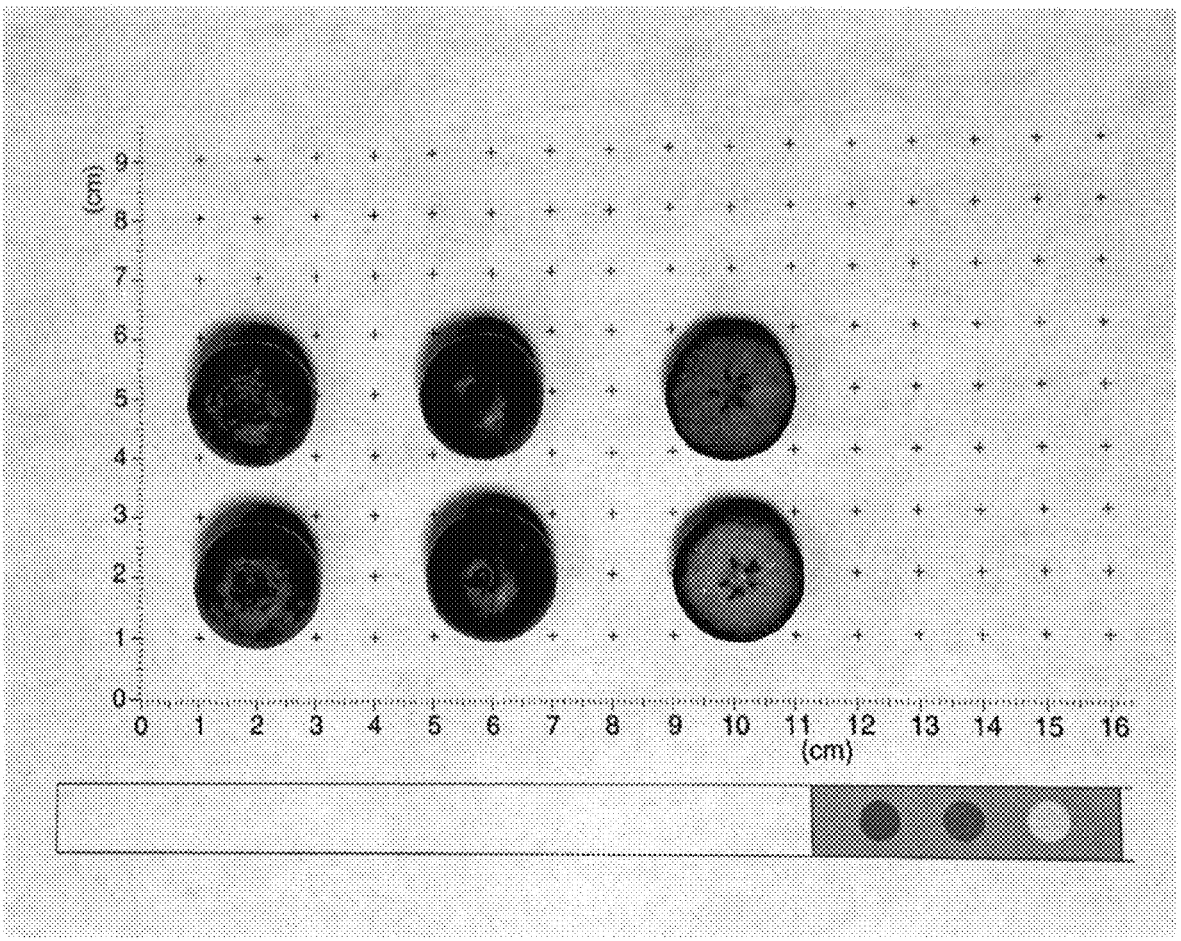
FIG. 4—Shows a close-up of mature 'FL17-141' fruit with a scale bar.
Figure 5:
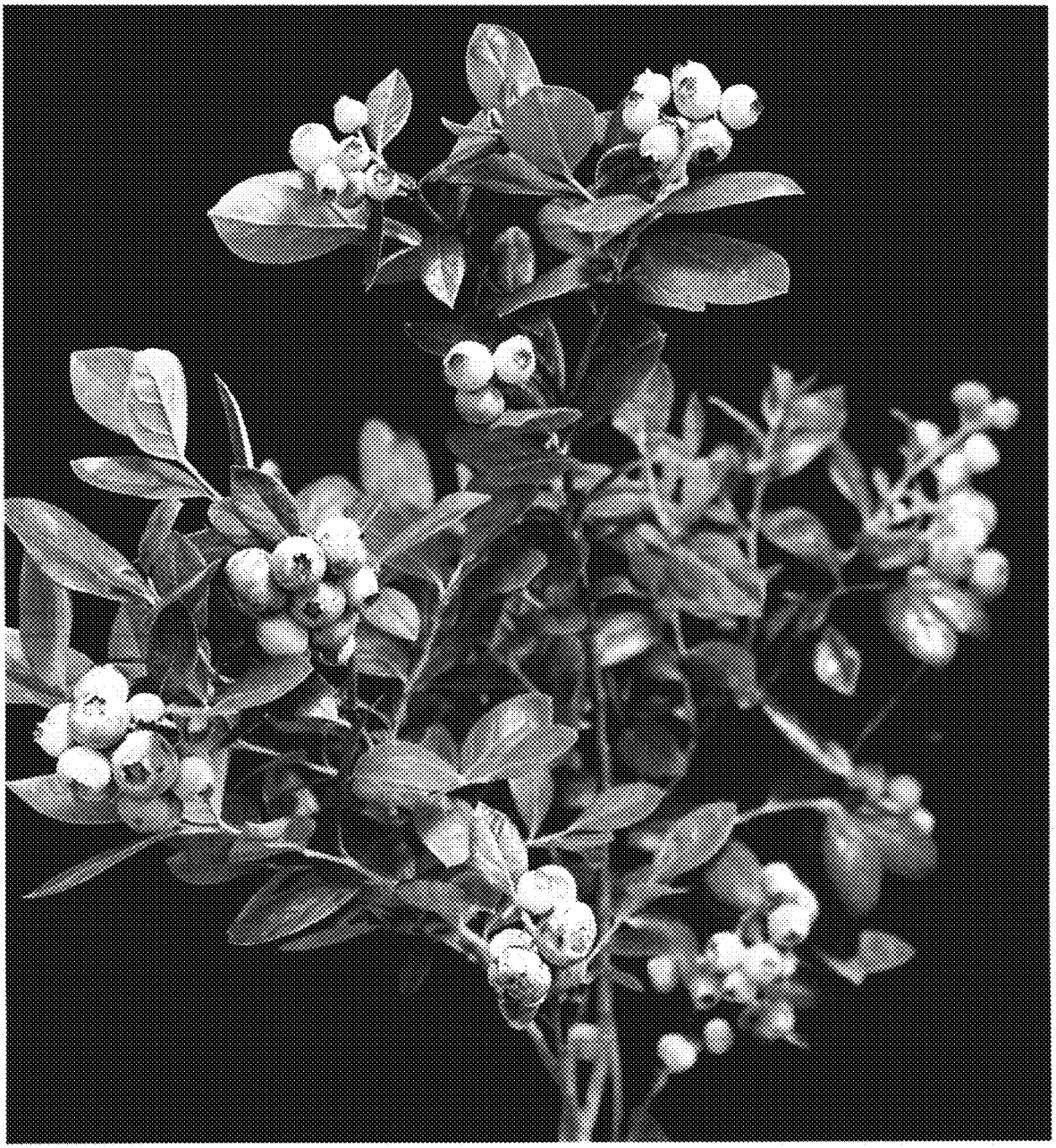
FIG. 5—Shows a close-up of ripening 'FL17-141' fruit on the plant
Figure 6:
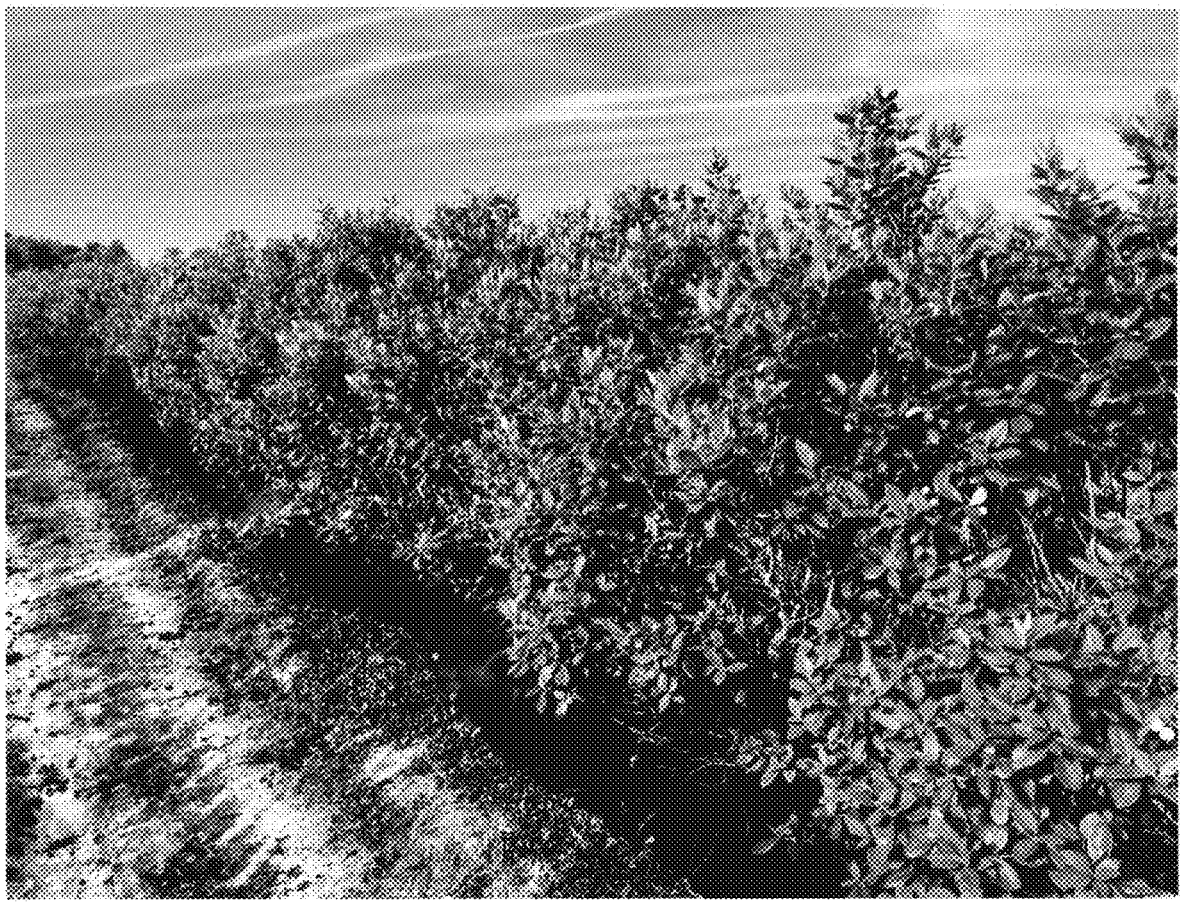
FIG. 6—Shows several five-year-old 'FL17-141' plants in May 5, 2023 with the vigorous, semi-upright architecture and its potential productivity.

The following detailed description sets forth distinctive characteristics of 'FL17-141'. The data that define these characteristics were collected from asexual reproduction plants established in Florida. The plant history was taken on a plot of plants growing in an experimental trial in Windsor, Florida. The plants were 5 years of age when the data was collected. Certain characteristics may vary with plant age. 'FL17-141' has not been observed under all possible environmental conditions, and the measurements given may vary when grown in different environments. Color descriptions are based on The Royal Horticultural Society (R.H.S.) Color Chart by The Royal Horticultural Society, London, 6th Edition, (2015). If any R.H.S. color designations below differ from the accompanying photographs, the R.H.S. color designations are accurate.

Classification:

*Family*.—Ericaceae.

*Botanical*.—*Vaccinium corymbosum* L.

*Common name*.—Southern Highbush Blueberry.

*Cultivar name*.—'FL17-141'.

Plant:

*Plant vigor*.—High.

*Growth habit*.—Semi-upright bush architecture.

*Plant height*.—1.6007 m on average for 5-year-old plant.

*Plant spread*.—1.7493 m on average for 5-year-old plant.

*Flower bud density* (*number*) *along flowering twigs in January*.—High.

*Twigginess*.—Medium High.

*Tendency toward evergreen-ness*.—High, Evergreen Candidate.

*Productivity*.—In northeast Florida, 'FL17-141' produces 5.2 kg/bush per season from plants 5 years old or when hand harvested.

*Chilling requirement*.—It has been observed producing high yields in years of chill (below 7° C.) around 100-150 in north Florida and 0-50 hours in south FL.

*Cold hardiness*.—'FL17-141' has been grown in temperate climates with extremely cold winter temperatures. Plants have survived winter freezes of −7° C. with minimal damage.

*Ease of propagation*.—'FL17-141' has only been propagated from softwood stem cuttings, where the rooting percentage is greater than 85% and comparable to other varieties.

Trunk and branches:

*Suckering tendency*.—Low to medium.

*Surface texture* (*of strong, 12-month-old shoots observed*).—Moderately smooth with minimal beaded texture (little to no presence of ridges and bark-like structures).

*Surface texture* (*of 3-year-old and older wood*).—Moderately rough with the presence of a beaded texture with minimal bark flaking.

*Color of new twigs observed in the field*.—Fan 3 Yellow-Green Group 146 Moderate Yellow Green C.

*Color of 3-year-old, rough-textured canes*.—Fan 4 Grey Group 201 Pinkish Grey D blended with hints of Fan 4 Greyed-Orange Group N167 Brownish Orange B and Fan 4 Greyed-Orange Group 166 Greyish Brown A.

*Internode length* (*strong, upright shoots*).—Mean of 12.89 mm.

Leaves:

*Leaf arrangement*.—Alternate, Fibonacci Spiral.

*Length* (*including petiole, from tip of petiole to end of blade*).—Mean of 5.281 cm.

*Width* (*at widest point*).—Mean of 3.066 cm.

*Petiole length*.—Mean of 4.02 mm.

*Petiole diameter*.—Mean of 1.78 mm.

*Leaf shape*.—Elliptic, slight falcate at leaf apex.

*Leaf base shape*.—Elliptic.

*Leaf venation pattern*.—Reticulate.

*Margin*.—Entire.

*Color*.—Upper surface: Fan 3 Green Group 137 Moderate Olive Green A. Lower surface: Fan 4 Greyed Green Group 191 Greyish Yellow-Green A. Leaf Vein Color: Fan 3 Yellow Green Group 145 Light Yellow-Green C. Leaf petiole color: Fan 3 Yellow Green Group 145 Light Yellow-Green B.

*Pubescence*.—Upper surface of leaves: Absent. Lower surface of leaves: Absent. Margins: Absent.

*Timing of vegetative bud burst* (*early, medium, late*).—Early.

*Relative time of leafing versus flowering*.—When not treated with hydrogen cyanamide in mid-winter, leafing occurs during flowering.

*Leaf glaucosity*.—High.

Flowers:

*Inflorescence* (*small, medium, large*).—Medium.

*Arrangement*.—Flowers are arranged in an alternate fashion with a spiral configuration along a branch with old and new leaves.

*Fragrance*.—Very slight floral fragrance.

*Shape*.—Oblate, slight oval with slight radiations along the length of the corolla.

*Flowering period*.—Mean date of 50% anthesis at Windsor, Florida is week 6-7 when not treated with hydrogen cyanamide.

*Cluster*.—Medium tight cluster.

*Number of flowers per cluster*.—Mean of 4.

*Pedicel*.—Length at time of anthesis: Mean of 5.48 mm. Color at time of anthesis (Non sun exposed side): Fan 3 Yellow-Green Group 145 Light Yellow Green B.

*Peduncle*.—Length at time of anthesis: Highly, variable, mean of 8.37 mm. Color at time of anthesis (Non sun exposed side): Fan 3 Yellow-Green group 145 Strong yellow green A.

*Calyx*.—Surface texture: Smooth with slight wax. Diameter: Mean of 5.44 mm. Color (outer surface, visible at the time of anthesis without removing the corolla tube): Fan 3 Green Group 133 Light Bluish Green C to Fan 3 Green Group 142 Brilliant Yellow-Green B on tips of calyx lobes. Flower receptacle color: Fan 3 Green Group N138 Brilliant Green D.

*Corolla*.—Diameter: mean of 9 mm. Length (from pedicel attachment point to corolla tip excluding the pedicel): Mean of 10.59 mm. Aperture diameter: Mean of 3.04 mm. Texture: Smooth with slight radiations. Color: Fan 4 White Group NN153 White C. Anthocyanin coloration in tube: Absent, none detected.

Reproductive organs:

*Style*.—Length (top of ovary to stigma tip): Mean of 8.55 mm. Color: Fan 3 Yellow-Green Group 145 Light Yellow Green C.

*Location of tip pf stigma relative to lip of the corolla*.—Stigma tip is approximately Even to 0.058 mm below the corolla lip.

*Anthers*.—

*Color*.—Fan 4 Greyed-Orange Group 167 Brownish-Orange B at the base and Fan 4 Greyed-Orange Group N167 Moderate Orange C toward the apex of the anther. Pollen: High. Pollen germination: Typically, greater 90%. Color: Fan 1 Yellow Group 8 Pale Yellow D. Filament length: 4.65 mm. Filament width: 1.4 mm.

*Self-fruitfulness*.—Low to medium. Planting in the field configurations that promote cross fertilization with other southern highbush varieties is recommended for all southern highbush blueberry plants grown in Florida.

Fruit:

*Mean date of* 50% *harvest in Citra, Florida*.—Apr. 10, 2023.

*Diameter of calyx aperture on mature berry*.—Mean of 5.8 mm.

*Size and shape of calyx lobes on mature berry*.—Very small, mostly flat and with some that are erect/out-curving. The calyx basin is shallow.

*Pedicel length on ripe berry*.—Mean of 4.89 mm.

*Detachment force for ripe berries* (*easy, medium, hard*) .—Easy.

*Fruit cluster density* (*sparse, medium, dense*).—Medium.

*Number of berries per cluster*.—Mean of 3.

*Fruiting type*.—Fruiting occurs on current season's shoots.

Berry:

*Cluster* (*tight, medium, loose*).—Medium.

*Weight* (*on well-pruned plants*).—(25 berries) Mean of 60.5 g.

*Height*.—Mean of 14.52 mm.

*Width*.—Mean of 19.20 mm.

*Shape*.—Oblate.

*Surface color of mature berries ripe on the plant*.—Fan 2 Violet-Blue Group 97 Very Pale Purplish Blue C.

*Intensity of fruit bloom*.—High.

*Surface color of ripe berry after polishing*.—Fan 4 Black Group 202 Dark Greyish Purple A.

*Immature berry color, with bloom*.—Fan 3 Yellow Green Group 144 Strong Yellow Green A.

*Immature berry color, without bloom*.—Fan 3 Yellow-Green Group 145 Light Yellow Green C.

*Flesh color*.—Fan 4 Grey-Green Group 195 Pale Yellow Green C.

*Surface wax*.—High and has high persistence.

*Pedicel scar*.—Small and dry. Mean of 1.55 mm.

*Firmness*.—Very firm. Mean 296.17 g/mm.

*Flavor*.—Balanced flavor between sweet and sour.

*Intensity of fruit sweetness*.—Medium to high.

*Texture*.—Good firm texture with non-mealy flesh. No stone cells present.

*Fruit storage quality*.—Fruit is firm and can be stored without shriveling, mold, or loss of firmness for 6 weeks stored at 4 degree C.

Seeds:

*Color of dried seeds*.—Fan 4 Greyed-Orange Group 166 Moderate Reddish Brown B.

*Weight of* 25 *well-developed dried seeds*.—Mean of 15.3 mg.

*Length of well-developed dried seeds*.—Mean of 1.85 mm.

*Width of well-developed dried seeds*.—Mean of 1.00 mm.

Use: Produces southern highbush blueberries suitable for hand harvest for the fresh fruit markets.

Resistance to diseases, insects, and mites: 'FL17-141' has grown vigorously and shows good bush survival in the field, with almost no young plants dying soon after planting. Reaction to the various fungal species that cause summer leaf spots (including rust) is lower than those of other southern highbush varieties. We have only observed lower levels of target spot (*Crynespora cassiicola*), but the plants seem tolerant to it. Fungicide applications may be needed after harvest to reduce foliar diseases and retain leaves into the fall for maximum flower bud set. In the field appears to be more tolerant than other southern highbush varieties to spider mites and blueberry chilly thrips (*Scirtothips dorsalis*). Susceptibility to typical blueberry insect and mite pathogens such as spotted wing drosophila (*Drosophila suzukii*), blueberry gall midge (*Dasineura oxycoccana*), blueberry flower thrips (*Frankliniella* spp), and blueberry bud mite (*Acalitus vaccini*) appear similar to other southern highbush cultivars.

What is claimed is:

1. A new and distinct variety of southern highbush blueberry plant named 'FL17-141', as illustrated and described herein.

* * * * *